US011147520B2

(12) United States Patent
Stefanyshyn et al.

(10) Patent No.: US 11,147,520 B2
(45) Date of Patent: Oct. 19, 2021

(54) METHOD AND SYSTEM FOR PREDICTING BIOMECHANICAL RESPONSE TO WEDGED INSOLES

(71) Applicant: UTI LIMITED PARTNERSHIP, Calgary (CA)

(72) Inventors: Darren John Stefanyshyn, Calgary (CA); Ryan Tomas Lewinson, Calgary (CA)

(73) Assignee: UTI Limited Partnership, Calgary (CA)

( * ) Notice: Subject to any disclaimer, the term of this patent is extended or adjusted under 35 U.S.C. 154(b) by 523 days.

(21) Appl. No.: 15/189,830

(22) Filed: Jun. 22, 2016

(65) Prior Publication Data
US 2016/0367199 A1 Dec. 22, 2016

Related U.S. Application Data

(60) Provisional application No. 62/183,055, filed on Jun. 22, 2015.

(51) Int. Cl.
| *A61B 5/00* | (2006.01) |
| *A61B 5/103* | (2006.01) |
| *A61B 5/11* | (2006.01) |
| *A43B 3/00* | (2006.01) |
| *G16H 50/20* | (2018.01) |
| *A43B 17/02* | (2006.01) |
| *A43B 7/14* | (2006.01) |

(52) U.S. Cl.
CPC ......... *A61B 5/7275* (2013.01); *A61B 5/1038* (2013.01); *A61B 5/112* (2013.01); *A61B 5/1121* (2013.01); *A61B 5/1127* (2013.01); *A61B 5/6807* (2013.01); *G16H 50/20* (2018.01); *A43B 3/0005* (2013.01); *A43B 7/142* (2013.01); *A43B 7/143* (2013.01); *A43B 7/1465* (2013.01); *A43B 17/023* (2013.01); *A61B 5/0077* (2013.01)

(58) Field of Classification Search
CPC ... A61B 5/7275; A61B 5/1038; A61B 5/1036; A61B 5/112; A61B 5/1121; A61B 5/1127; A61B 5/6807; A43B 3/0005; A43B 17/02; A43B 17/023
See application file for complete search history.

(56) References Cited

U.S. PATENT DOCUMENTS

2005/0261609 A1* 11/2005 Collings ............... A43B 3/0005
600/592
2014/0343460 A1* 11/2014 Evans, III .............. A61B 5/112
600/595

(Continued)

OTHER PUBLICATIONS

Nester et al., "Effect of foot orthoses on the kinematics and kinetics of normal walking gait", Gait and Posture, vol. 17, Issue 2, Apr. 2003, pp. 180-187. (Year: 2003).*

(Continued)

*Primary Examiner* — Devin B Henson
(74) *Attorney, Agent, or Firm* — Bennett Jones LLP

(57) ABSTRACT

The present invention relates to methods and systems for predicting biomechanical response to wedged insoles. In accordance with one aspect, a method for predicting a biomechanical response to a wedged insole is provided. In a further aspect, a system for predicting a biomechanical response to wedged insole is provided.

14 Claims, 2 Drawing Sheets

(56) References Cited

U.S. PATENT DOCUMENTS

2016/0210679 A1* 7/2016 Rohr ............... A61B 5/0077
2017/0042467 A1* 2/2017 Herr ............... A61B 5/6828

OTHER PUBLICATIONS

Hinman et al. "Lateral Wedges in Knee Osteoarthritis: What Are Their Immediate Clinical and Biomechanical Effects and Can These Predicta Three-Month Clinical Outcome?", Arthritis & Rheumatism, vol. 59, No. 3, Mar. 2008, pp. 408-415. (Year: 2008).*

Fisher et al. "In Healthy Subjects without Knee Osteoarthritis, the Peak Knee Adduction Moment Influences the Acute Effect of Shoe Interventions Designed to Reduce Medial Compartment Knee Load", Journal of Orthopaedic Research, vol. 25, Issue 4, Apr. 2007, pp. 540-546. (Year: 2007).*

Public Health Agency of Canada. Arthritis in Canada: An Ongoing Challenge. Ottawa, ON; 2012:124.

Reeves ND, Bowling FL. Conservative biomechanical strategies for knee osteoarthritis. Nat Rev Rheum. 2011;7:113-122.

Sharma L, Hurwitz DE, Thonar EJ, Sum JA, Lenz ME, Dunlop DD, et al. Knee adduction moment, serum hyaluronan level, and disease severity in medial tibiofemoral osteoarthritis. Arthritis Rheum. 1998;41:1233-1240.

Miyazaki T, Wada M, Kawahara H, Sato M, Baba H, Shimada S. Dynamic load at baseline can predict radiographic disease progression in medial compartment knee osteoarthritis. Ann Rheum Dis 2002;61:617-622.

Bennell KL, Bowles KA, Payne C, Cicuttini F, Williamson E, Forbes A, et al. Lateral wedge insoles for medial knee osteoarthrtis: 12 month randomised controlled trial. BMJ 2011;342:d2912.

Kerrigan DC, Leias JL, Goggins J, Merriman GJ, Kaplan RJ, Felson DT. Effectiveness of a lateral-wedge insole on knee varus torque in patients with knee osteoarthritis. Arch Phys Med Rehabil. 2002;83:889-893.

Chapman GJ, Parkes MJ, Forsythe L, Felson DT, Jones RK. Ankle motion influences the external knee adduction moment and may predict who will respond to lateral wedge insoles?: an ancillary analysis from the SILK trial. Osteoarthritis Cartilage. In Press.

Hinman RS, Bowles KA, Metcalf BB, Wrigley TV, Bennell KL. Lateral wedge insoles for medial knee osteoarthritis effects on lower limb biomechanics. Clin Biomech. 2012;27:27-33.

Lewinson RT, Collins KH, Vallerand IA, Wiley JP, Woodhouse LJ, Reimer RA, et al. Reduced knee joint loading with lateral and medial wedge insoles for management of knee osteoarthritis: a protocol for a randomized controlled trial. BMC Musculoskelet Dis. 2014;15:405.

Kakihana W, Akai M, Nakazawa K, Naito K, Torii S. Inconsistent knee varus moment reduction caused by lateral wedge in knee osteoarthritis. Am J Phys Med Rehab. 2007;86:446-454.

Winter DA. Biomechanics and Motor Control of Human Movement. 4th ed. Hoboken, NJ: John Wiley & Sons; 2009.

Lewinson RT, Worobets JT, Stefanyshyn DJ. Knee abduction angular impulses during prolonged running with wedged insoles. Proc Inst Mech Eng H. 2013;227:811-814.

Hinman RS, Payne C, Metcalf BR, Wrigley TV, Bennell KL. Lateral wedges in knee osteoarthritis: What are their immediate clinical and biomechanical effects and can these predict a three-month clinical outcome? Arthritis Rheum. 2008;59:408-415.

Kadaba MP, Ramakrishnan HK and Wooten ME. Measurement of lower extremity kinematics during level walking. J Orthop Res 1990;8:383-392.

Lewinson RT, Worobets JT, Stefanyshyn DJ. The relationship between maximal hip abductor strength and resultant loading at the knee during walking Proc Inst Mech Eng H. 2014;228:1258-1263.

Robertson DGE, Caldwell GE, Hamill J, Kamen G, Whittlesey S. Research methods in biomechanics. Windsor, ON, Canada: Human Kinetics, 2004.

Dempster W. Space requirements of the seated operator. Ohio: Wright-Patterson Air Force Base; 1955:183-200.

Clauser CE, McConville JT, Young JW. Weight, volume and center of mass of segments of the human body. Ohio Wright-Patterson Air Force Base; 1969:42-61.

Allen DM. The relationship between variable selection and data augmentation and method for prediction. Technometrics. 1974;16:125-127.

* cited by examiner

METHOD AND SYSTEM FOR PREDICTING BIOMECHANICAL RESPONSE TO WEDGED INSOLES

FIELD OF THE INVENTION

The present invention relates to a method and system for predicting biomechanical response to wedged insoles.

BACKGROUND

Knee osteoarthritis (OA) is one of the most common musculoskeletal injuries, and is characterized by elevated frontal-plane knee joint loading (i.e. external knee adduction moments) during walking.[1,2] These moments, often calculated by inverse dynamics, represent the resultant load acting on the knee joint in the frontal-plane during gait. Indeed, increased frontal-plane knee moments have been associated with increased knee OA pain and greater OA severity.[3,4] Consequently, reducing these moments has become an important strategy for clinical management of knee OA.

One of the most common approaches to reducing these frontal plane moments has been to apply wedged footwear insoles or orthotics bilaterally within the patient's shoe.[1,5,6] In biomechanical studies, wedged insoles have been shown to reduce knee adduction moments by 6-15% for most patients; however, for approximately 33% of patients, a negative biomechanical response is observed, i.e. an increase to the knee adduction moment.[7] This fact may contribute to why clinical studies have often shown mixed results in terms of the clinical efficacy of wedged insoles.

Given some patients may not respond, biomechanically, to a wedged insole, there has recently been increased interest in being able to identify, prior to insole prescription, which patients are likely to benefit in a biomechanical sense from a wedged insole intervention.[7,8] In research settings, this is being done by only including biomechanical responders in study designs (i.e. those who experience reduced knee adduction moments with the intervention),[7] or in testing a variety of insole types to optimize the biomechanical result (i.e. ensure a reduction to the knee adduction moment).[9] However, in clinical settings, where expensive gait analysis equipment is typically unavailable, there is currently no way to predict if a patient is likely to experience a positive biomechanical response to a wedged insole.

Research studies have found that center of pressure positions beneath the foot,[8,10] knee joint lever arms,[8] or ankle angles at touchdown,[7] may be weak-moderate predictors of biomechanical efficacy; however, these methods all require a detailed and expensive gait analysis setup. For a prediction method to be clinically relevant and useful in community settings, the method should ideally: be small in design so as not to take up clinic space; have the potential to collect relevant data with inexpensive equipment such that it is affordable by specialty clinics; support relatively rapid data collection and analysis time; and be a strong predictor of the expected biomechanical response to a wedged insole.

SUMMARY OF THE INVENTION

The present invention generally relates to a method and system for predicting biomechanical response to wedged insoles.

In one aspect, the present invention comprises a method for predicting a biomechanical response to a wedged insole that comprises recording vertical load of an individual taking a step, or similar movement, in neutral footwear; recording vertical load of the individual taking a step, or similar movement in one or more types of wedged footwear; recording lower leg frontal-plane positions of the individual for each type of footwear; identifying a time at which the vertical load is at its maximum during a stance phase for each type of footwear; obtaining lower leg position data at the time for each type of footwear; calculating mediolateral positions of the lower leg and foot center of mass for each type of footwear; calculating percent change in the mediolateral positions of the wedged footwear relative to the neutral footwear; and applying one or more regression equations to predict a knee adduction moment response for the individual.

In another aspect, the present invention comprises a system for predicting a biomechanical response for an individual that comprises means for recording a vertical load for an individual taking a step, or similar movement, in neutral footwear and in one or more types of wedged footwear; means for recording lower leg frontal-plane positions of the individual for each type of footwear; means for identifying a time at which the vertical load is at its maximum during a stance phase and for obtaining leg position at that time; means for calculating percent change in mediolateral positions of wedged footwear relative to neutral footwear; and means for predicting a knee adduction moment response for the individual.

In a further aspect, the present invention comprises a method for predicting knee adduction moment response to wedged insoles that comprises recording a vertical ground reaction force of an individual taking a step, or similar movement, in neutral footwear and in one or more types of wedged footwear comprising lateral wedged footwear and medial wedged footwear; recording lower leg frontal-plane positions of the individual for each type of footwear; identifying a time at which the vertical ground reaction force is at its maximum during a first 50% of stance phase for each type of footwear, and obtaining lower leg position data at the time of the peak for each type of footwear; calculating mediolateral positions of the lower leg for each type of footwear; calculating percent change in the mediolateral positions of wedged footwear relative to neutral footwear; applying one or more regression equations to predict a knee adduction moment response for the individual; and selecting a wedged or non-wedged footwear based on predicted knee adduction moment response.

Additional aspects will be apparent in view of the description, which follows. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention will now be described by way of an exemplary embodiment with reference to the accompanying simplified, diagrammatic, not-to-scale drawings. Any dimensions provided in the drawings are provided only for illustrative purposes, and do not limit the invention as defined by the claims. In the drawings:

DETAILED DESCRIPTION OF THE INVENTION

Figure 1:
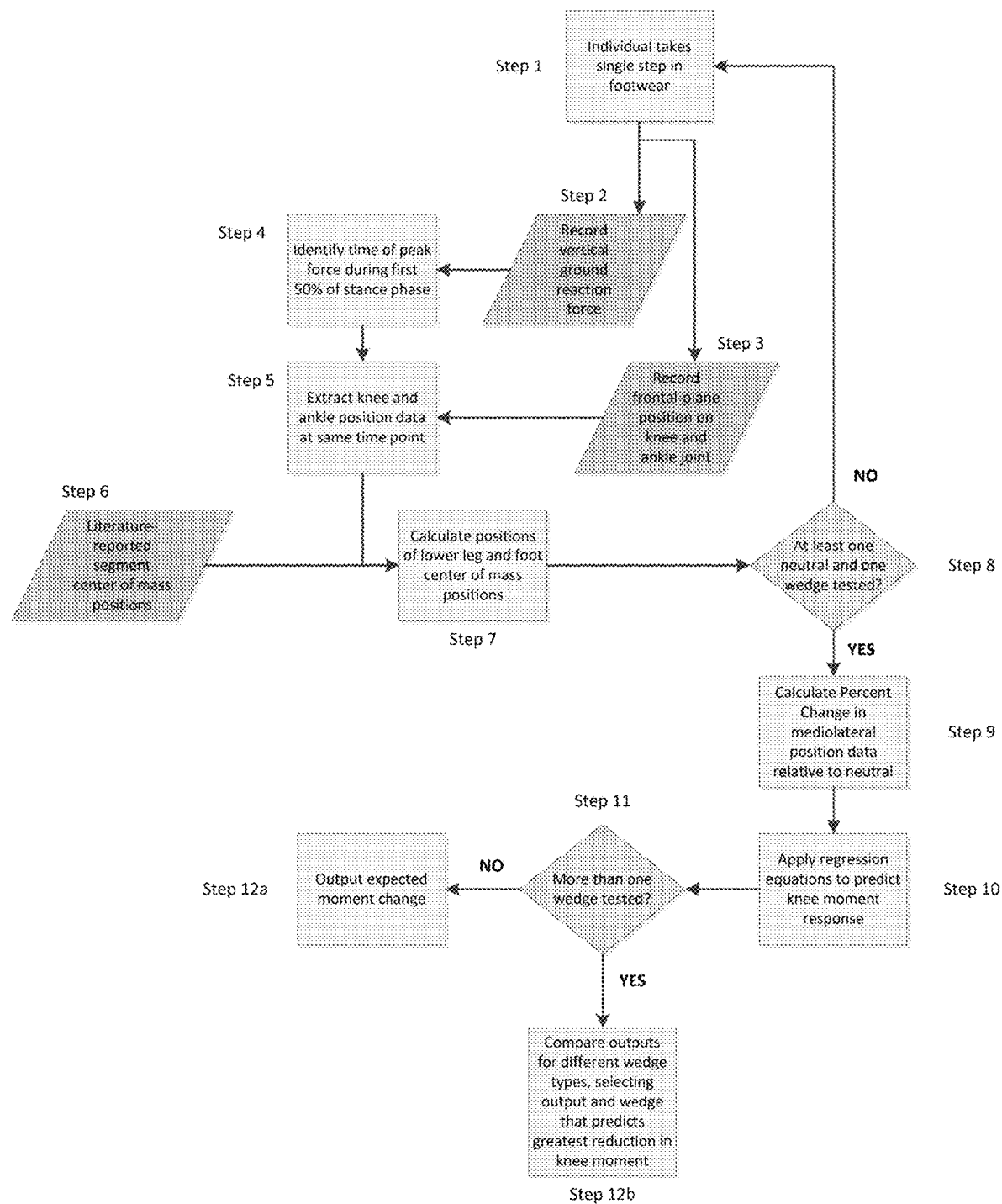
FIG. 1 is a process flow chart of a method according to one embodiment of the present invention.

The present invention aims to provide a method for predicting the expected change in moment ("KAM") with a wedged insole intervention. The method uses two dimensional data to generate a prediction.

A method for predicting the expected change to the frontal-plane knee joint moment during walking with a wedged insole is described herein. Based on Newton-Euler equations of motion,[11] applied to a rigid free body diagram of the lower leg segment, it can be seen that the variables that contribute to the magnitude of the knee joint moment include: (i) inertial parameters of the lower leg, angular velocities and accelerations of the lower leg, (ii) forces acting at the ankle and knee, (iii) moments acting at the ankle, and (iv) lever arms from the ankle and knee joints to the segment centers of mass. By focusing exclusively on the mediolateral components of the lever arms of the lower leg at a single time point during a movement similar to walking, the expected frontal-plane knee moment change may be predicted.

The method of the present invention is illustrated by way of the following example:

Participants

Fifteen healthy individuals without any history of musculoskeletal injury (10 males, 5 females, mean±SD age of 24.9±4.5 years, height of 174.7±10.1 cm, mass of 72.1±14.0 kg), and 19 individuals with medial knee osteoarthritis (5 males, 14 females, mean±SD age of 59.8±6.7 years, height of 170.5±10.7 cm, mass of 89.7±23.6 kg), as diagnosed by a physician according to the American College of Rheumatology radiographic and clinical criteria, participated in the study.

Data Collection

Three retroreflective tracking markers were secured to each of the foot (i.e. shoe) and shank (i.e. lower leg) segments. For healthy individuals, this was done on the right lower limb. For individuals with knee OA, this was done on the more symptomatic limb.

In a randomly assigned order, participants completed 5 trials walking along a 20 m runway in the control condition (participant's own shoes), in a medial wedge condition, and in a lateral wedge condition, in both cases where a 6 mm wedge was applied bilaterally beneath the sock liner of the participant's own shoes.[9,12] A force platform (Kistler Group, Winterthur Switzerland) mounted flush with the lab floor collected ground reaction force data in three dimensions at a frequency of 2400 Hz and an 8 camera Motion Analysis system (Motion Analysis Corp., Santa Rosa, Calif.) collected 3D retroreflective marker trajectories at a frequency of 240 Hz during each trial. Photocells placed 1.9 m apart were used to monitor gait speed for each trial, where healthy participants maintained speeds of 1.5 m/s (±5%) and OA individuals maintained speeds of 1.3 m/s (±5%) for each trial. Different gait speeds were chosen as individuals with knee OA tend to walk slower than uninjured individuals.[13,14] If the speed requirements were not met, or if the participant did not land on the center of the force platform with the lower limb of interest, the trial was repeated until a total of 5 successful trials were obtained.

Additionally, each participant completed 5 single step trials with each of the three footwear conditions (FIG. 1, Step 1). These trials were not speed controlled, and consisted of the participant standing in a neutral position with both feet just in front of the force plate, and then taking a single step over the force plate. This included landing and pushing off on the plate with their lower limb of interest and then returning to a neutral standing position on the other side of the force plate.

Finally, additional retroreflective markers were placed over the medial and lateral malleoli and epicondyles of each participant, and a standing neutral trial was collected, where the participant stood on the force platform in the anatomical position. This was done for each of the footwear conditions for each participant.

Data Processing

Kinematic and kinetic data for the walking, single step and neutral trials were imported into KinTrak™ (v7.0, University of Calgary, Calgary, AB; http://www.ucalgary.ca/hpl/software/kintrak/getting), and smoothed using fourth order Butterworth low-pass filters with cutoff frequencies of 12 Hz and 50 Hz, respectively.[12,15] Alternatively, Visual3D™, by C-Motion Inc., may be used in lieu of KinTrak™.

From the neutral trials, the knee and ankle joint centers were defined as the point about 50% of the distance between the epicondyle and malleoli markers, respectively, in the x, y and z directions.[16] These locations were used to define segment lengths for the foot and shank. Segment center of mass locations, segment masses and segment moments of inertia were taken from the literature, or calculated from the neutral trial using proportions defined in the literature.[17,18] This was done for each neutral trial collected, and these lower extremity models were then applied to their associated walking and single step trials (e.g. lateral wedge neutral trial applied to walking and single step lateral wedge trials for each participant).

For walking and single step trials, stance phase was defined as the period from foot touchdown to foot takeoff, which were defined as the rising cross of 9.81 N and the falling cross of 9.81 N, both of the vertical ground reaction force.

In walking trials, external knee adduction moments were calculated during stance phase using a standard Newton-Euler inverse dynamics approach,[11] where forces and moments were first resolved for the ankle joint, and then ankle joint reaction kinetics were applied to the shank segment to resolve forces and moments at the knee. The peak knee adduction moment that occurred during the first 50% of stance phase was extracted for each trial. For each participant, the mean peak knee adduction moment was calculated across trials for each footwear condition. This approach represented the classical analysis approach that yielded the knee adduction moments during walking.

For single step trials, the mediolateral kinematic data and vertical ground reaction forces were studied (FIG. 1, Steps 2 and 3). First, the time at which the vertical ground reaction force was at its maximum within the first 50% of stance phase was identified (FIG. 1, Step 4). This time point was chosen because it roughly coincides with the time at which the first peak knee adduction moment occurs, and is an easily identifiable marker on the vertical ground reaction force curve. At this time point, the mediolateral positions of the knee joint center, shank center of mass, ankle joint center and foot center of mass were extracted for each trial (FIG. 1, Steps 5, 6 and 7). For each participant, the mean mediolateral positions of each marker were then calculated across trials for each footwear condition. This approach represented the new method that was used to predict actual knee adduction moments during walking. In alternate embodiments, a similar approach may be implemented so as to detect loading during the second half of stance, such as for example, finding the peak load during the second half of stance. In further embodiments, certain percentage of time during stance phase may also be used. For example, the peak load may normally happen between 20% to 30% of stance phase, and the method of the present invention may be used for reasonably estimating insole effects based on using the time point at 20% to 30%, for example, rather than identifying the peak load.

Statistical Analysis

All statistical analyses were performed in MATLAB r2015a (MathWorks Inc., Natick, Mass.) at a significance level of 0.05. From the mean data for each participant, the percent change in walking knee adduction moment, and percent change in single step marker positions were determined for each footwear condition. These percent changes were expressed relative to the neutral condition (FIG. 1, Steps 8 and 9).

Four multiple regression equations were then developed; two for the healthy study group, and two for the knee OA study group. The first multiple regression equation ("MarkersMW") of each group studied changes induced by the medial wedge insole, where percent changes to the single step mediolateral knee joint center, shank center of mass, ankle joint center, and foot center of mass positions were included as independent variables, and percent change in peak knee adduction moment during walking induced by the medial wedge was the dependent variable. The second multiple regression equation ("MarkersLW") of each group studied changes induced by the lateral wedge insole, where percent changes to the single step mediolateral knee joint center, shank center of mass, ankle joint center, and foot center of mass positions were included as independent variables, and percent change in peak knee adduction moment during walking induced by the lateral wedge was the dependent variable. Therefore, in both cases above, single step data were used to predict actual knee adduction moments during walking.

Given the low sample sizes used to develop the regression equations, a simulation test was conducted whereby the stability of these regression models, or the ability to predict future data, was evaluated. This was done by systematically removing each individual participant from the calculation of the MarkerMW and MarkerLW equations, and re-developing the equations with n-1 observations. Then, the data from the removed subject were applied to the new equation to output their predicted change in knee adduction moment during walking (FIG. 1, Step 10). This was done for all participants in both wedge conditions. This procedure allows for the computation of the PRESS Statistic, and the corresponding Predicted R-Squared ($r^2_p$) value which is an indication of how the model will hold to predictions with new, future data.[19] Therefore, the $r^2_p$ indicates an exploratory measure that describes the model's current ability to predict new values, whereas the regression coefficients described above represent the model's relationship to the variables evaluated. Correspondingly, the original regression coefficients are important features.

Based on the predicted walking knee adduction moment changes output by the simulation, based on single step data, an algorithm was developed that would either indicate "lateral wedge," "medial wedge," or "no wedge" as a recommendation for each participant (see FIG. 1, steps 11, 12a and 12b). Specifically, the insole that was predicted to reduce knee adduction moments the most during walking was always selected as the output. In cases where a lateral wedge or medial wedge recommendation was made, this recommendation was classified as correct if the recommended insole did indeed reduce the knee adduction moment during the walking trials, as determined by comparing predicted change values to actual knee adduction moment changes that occurred in the walking trials, and incorrect if the recommended insole increased knee adduction moments during the walking trials, as determined by comparing predicted change values to actual knee adduction moment changes that occurred in the walking trials. In cases where no insole was recommended (i.e. neither insole was predicted to reduce the knee adduction moment), this was classified as a correct recommendation if indeed neither insole type reduced knee adduction moments during walking, as determined by comparing predicted change values to actual knee adduction moment changes that occurred in the walking trials, and classified as incorrect if in fact one of the insole types would have reduced knee adduction moments.

Results

For the healthy individuals, a significant relationship was found for MarkerMW ($R^2$=0.67, p=0.016), and also for MarkerLW ($R^2$=0.72, p=0.008) for predicting the change in knee adduction moment induced by a wedge using mediolateral lower extremity marker positions. For the knee OA individuals, a significant relationship was found for MarkerMW ($R^2$=0.54, p=0.020), and also for MarkerLW ($R^2$=0.52, p=0.026) for predicting the change in knee adduction moment induced by a wedge using mediolateral lower extremity marker positions.

Figure 2:
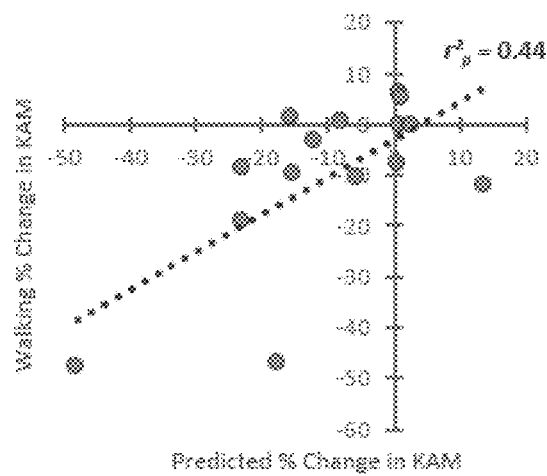
FIG. 2 are graphical representations of the predicted knee adduction moment changes derived from a simulation experiment conducted according to an embodiment of the method of the present invention.
Figure 2:
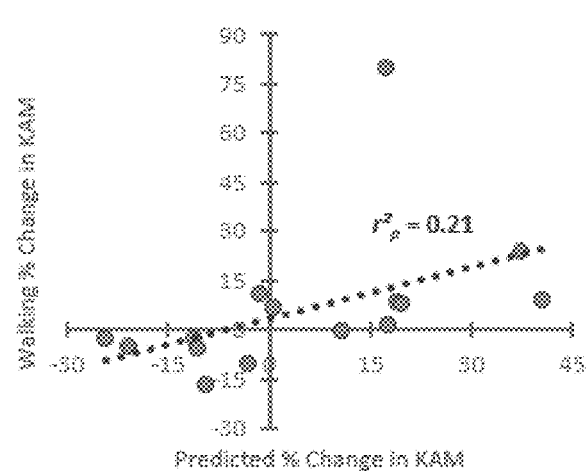
Figure 2:
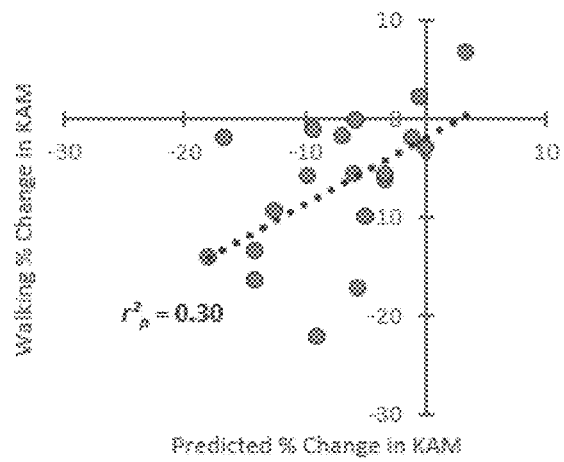
Figure 2:
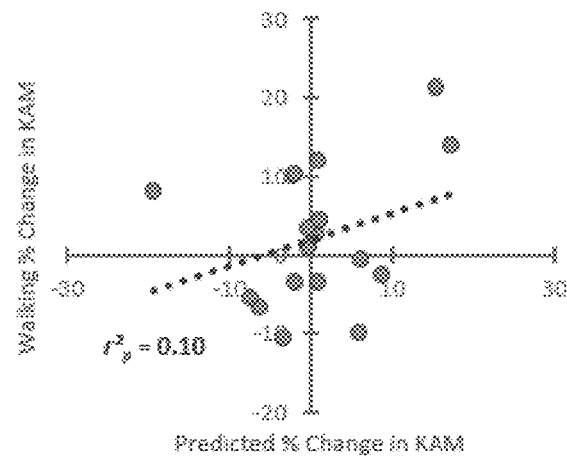

When comparing predicted knee adduction moment changes from the regression equations, against actual knee adduction moment changes as determined from the walking trials, a significant relationship was found in the healthy study group for lateral wedge induced changes using MarkerLW ($r^2_p$=0.44, p=0.007), and a near significant relationship was found for medial wedge induced changes using MarkerMW ($r^2_p$=0.21, p=0.084). A significant relationship was found in the knee OA group for lateral wedge induced changes using MarkerLW ($r^2_p$=0.30, p=0.016), but no significant relationship was found for medial wedge induced changes using MarkerMW ($r^2_p$=0.10, p=0.19). These results are shown in FIG. 2.

When utilizing predicted outputs for both the MarkerLW and MarkerMW equations to identify the recommended wedged insole condition for each participant, one could correctly identify, for 12/15 healthy individuals and 17/19 knee OA individuals, the correct recommendation (either insole or no insole) to ensure knee adduction moments were either reduced, or prevented from increasing. In the cases where the algorithm made incorrect recommendations in the healthy group, the algorithm suggested "no insole" on one occasion when in fact a lateral wedge would have reduced the knee adduction moment, and recommended "lateral wedge" on two occasions when this would have in fact resulted in an increased knee adduction moment. In the knee OA group, there was one case where no insole was recommended when in fact a medial wedge would have been the best recommendation, and one case where a medial wedge was recommended when in fact no insole would have been the correct recommendation.

Discussion

The present invention discloses a method for predicting the biomechanical effects of wedged insoles during walking. The experiment confirmed that mediolateral positions of the lower leg at the instant of the maximum vertical ground reaction force during the first half of stance during a single step movement are related to change in knee adduction moment during walking induced by a wedged insole intervention. There are significant relationships for predicting the effects of medial and lateral wedge insoles for both healthy and knee osteoarthritic individuals.

Previous research has suggested relationships between change in knee adduction moment during walking and change in center of pressure position, change in frontal-plane ankle joint angle or change in knee joint center to center of pressure lever arm magnitudes;[7,8] however, these associations were typically quite low, and were developed using walking multi-axis data collection methods during controlled walking movements. Thus, the large $R^2$ values presented for the four regression equations that used uniaxial data, during a simpler and less controlled movement are noteworthy.

The use of uniaxial force measurement in the present method may be more cost-effective than multi-axis systems for computing the center of pressure beneath the foot. Since the force variable chosen is a distinguishable peak in the vertical ground reaction force, identification of this peak and associated time point using force plates that do not have a high sampling frequency may also be possible. Since the present method can use 2D kinematic data, frontal-plane positions of the lower leg, and during a fairly slow movement (i.e. single step), a relatively simple system may be used for collection of this data such as a standard video camera or an X-Box® Kinect® system. In alternate embodiments, inertial sensors, located on the lower leg, such as, for example, at or about a knee location and an ankle location of a user may be used for collecting lower leg position data. In alternate embodiments, "vision" software for limb detection, such as, for example, Microsoft Kinect® or other similar products, may be used to detect limb positions without markers or inertial sensors.

In one sample embodiment, a participant wears an identification band around their knee and ankle to signify joint locations from which the segment center of mass positions are computed using literature data. Then the participant takes a series of single steps while a video system collects frontal plane motion data and a uniaxial force platform synchronously collects vertical forces (not unlike a digital scale with a real-time feed). At the instant of maximal vertical force, which may be easily detected by a simple computer algorithm (e.g. the MATLAB® "findpeaks" function), the limb positions are obtained. The participant then changes their footwear type (e.g. a wedged insole) and the data collection is repeated in the manner as with the previous footwear type. The change in the collected data between the two footwear types is calculated and input into standardized regression equations to yield the predicted change in knee adduction moment. In other embodiments, alternate force platforms, such as a two-dimensional or three-dimensional force platform, may be used in the collection of vertical forces. It can be appreciated that the present invention is not necessarily restricted to a vertical "force". In alternate embodiments, other measurements of vertical loading may be used, such, for example, peak pressure during stance phase.

While significant relationships were found for all four regression equations, the lateral wedge equations are particularly useful for evaluating the predicted $r_p^2$ values. For the lateral wedge equations, error rates (11-13%) were lower than those typically reported in the literature when all subjects are given a lateral wedge (33%)[7].

One source of error in the example may be that marker positions at the knee and ankle were reapplied with each new footwear condition rather than remaining fixed to the participant throughout all conditions and trials. While markers were placed on each participant by the same researcher in all occasions, slight changes in marker positions are still possible, which would introduce error to the joint center locations. This error may be mitigated by ensuring markers remain fixed to the participant during all trials and footwear conditions.

The present invention provides a method for predicting changes to the knee adduction moment during walking resulting from a wedged insole intervention using mediolateral position data of the lower extremity during a single step movement. This method may allow for simple biomechanical data collection and analysis in clinical settings, thereby allowing for a personalized approach to wedged insole prescription.

In accordance with the present invention, other closely related variables would be understood to include frontal plane knee angular impulse, or the frontal plane knee moment at any point in time. As well, a frontal plane moment may be that of internal abduction, or external adduction, for example.

As will be apparent to those skilled in the art, various modifications, adaptations and variations of the foregoing specific disclosure can be made without departing from the scope of the invention claimed herein.

REFERENCES

1) Public Health Agency of Canada. Arthritis in Canada: An Ongoing Challenge. Ottawa, ON; 2012:124.

2) Reeves N D, Bowling F L. Conservative biomechanical strategies for knee osteoarthritis. Nat Rev Rheum, 2011; 7:113-122.

3) Sharma L, Hurwitz D E, Thonar E J, Sum J A, Lenz M E, Dunlop D D, et al. Knee adduction moment, serum hyaluronan level, and disease severity in medial tibiofemoral osteoarthritis. Arthritis Rheum. 1998; 41:1233-1240.

4) Miyazaki T, Wada M, Kawahara H, Sato M, Baba H, Shimada S. Dynamic load at baseline can predict radiographic disease progression in medial compartment knee osteoarthritis. Ann Rheum Dis 2002; 61:617-622.

5) Bennell K L, Bowles K A, Payne C, Cicuttini F, Williamson E, Forbes A, et al. Lateral wedge insoles for medial knee osteoarthritis: 12 month randomised controlled trial. BMJ. 2011; 342:d2912.

6) Kerrigan D C, Lelas J L, Goggins J, Merriman G J, Kaplan R J, Felson D T. Effectiveness of a lateral-wedge insole on knee varus torque in patients with knee osteoarthritis. Arch Phys Med Rehabil. 2002; 83:889-893.

7) Chapman G J, Parkes M J, Forsythe L, Felson D T, Jones R K. Ankle motion influences the external knee adduction moment and may predict who will respond to lateral wedge insoles?: an ancillary analysis from the SILK trial, Osteoarthritis Cartilage. In Press.

8) Hinman R S, Bowles K A, Metcalf B B, Wrigley T V, Bennell K L. Lateral wedge insoles for medial knee osteoarthritis: effects on lower limb biomechanics. Clin Biomech. 2012; 27:27-33.

9) Lewinson R T, Collins K H, Vallerand I A, Wiley J P, Woodhouse L J, Reimer R A, et al. Reduced knee joint loading with lateral and medial wedge insoles for management of knee osteoarthritis: a protocol for a randomized controlled trial. BMC Musculoskelet Dis. 2014; 15:405.

10) Kakihana W, Akai M, Nakazawa K, Naito K, Torii S. Inconsistent knee varus moment reduction caused by lateral wedge in knee osteoarthritis. Am J Phys Med Rehab. 2007; 86:446-454.

11) Winter D A, Biomechanics and Motor Control of Human Movement, 4th ed. Hoboken, N.J.: John Wiley & Sons; 2009.

12) Lewinson R T, Worobets J T, Stefanyshyn D J. Knee abduction angular impulses during prolonged running with wedged insoles, Proc Inst Mech Eng H. 2013; 227:811-814.

13) Hinman R S, Payne C, Metcalf B R, Wrigley T V, Bennell K L. Lateral wedges in knee osteoarthritis: What are their immediate clinical and biomechanical effects and can these predict a three-month clinical outcome? Arthritis Rheum. 2008; 59:408-415.

14) Kadaba M P, Ramakrishnan H K and Wooten M E. Measurement of lower extremity kinematics during level walking. J Orthop Res. 1990; 8:383-392

15) Lewinson R T, Worobets J T, Stefanyshyn D J. The relationship between maximal hip abductor strength and resultant loading at the knee during walking. Proc Inst Mech Eng H. 2014; 228:1258-1263.

16) Robertson D G E, Caldwell G E, Hamill J, Kamen G, Whittlesey S. Research methods in biomechanics. Windsor, ON, Canada: Human Kinetics, 2004

17) Dempster W. Space requirements of the seated operator. Ohio: Wright-Patterson Air Force Base; 1955:183-200.

18) Clauser C E, McConville J T, Young J W. Weight, volume, and center of mass of segments of the human body. Ohio: Wright-Patterson Air Force Base; 1969:42-61.

19) Allen D M. The relationship between variable selection and data augmentation and method for prediction. Technometrics. 1974; 16:125-127.

What is claimed is:

1. A method for predicting a biomechanical response to a wedged insole, consisting of:
   recording, using a flush floor-mounted two-dimensional force platform, data consisting of vertical load data of an individual taking a single step in neutral footwear;
   recording, using the platform, vertical load data of the individual taking another single step in one or more types of wedged footwear;
   recording lower leg frontal-plane positions of the individual for each type of footwear;
   identifying a time when the vertical load is at its maximum during a stance phase for each type of footwear;
   calculating mediolateral positions of the lower leg and foot center of mass for each type of footwear using the lower leg frontal-plane positions at the time when the vertical load is at its maximum during the stance phase for each type of footwear;
   calculating percent change in the mediolateral positions of the wedged footwear relative to the neutral footwear; and
   applying one or more regression equations to predict a knee adduction moment response for the individual.

2. The method of claim 1, wherein the one or more types of wedged footwear comprises lateral wedged footwear and medial wedged footwear, and the neutral footwear comprises non-wedged footwear.

3. The method of claim 1, wherein the stance phase is a first 50% of stance phase or a second 50% of stance phase, the vertical load is vertical ground reaction force, and the time is a peak time at which the vertical ground reaction force is at its maximum during the stance phase.

4. The method of claim 3, wherein a computer algorithm is used to detect a peak time at which vertical ground reaction force is at its maximum.

5. The method of claim 1, wherein the platform is comprised of a pressure mat or a uniaxial force platform.

6. The method of claim 1, wherein markers are positioned at one or more lower leg positions of the individual and a video system is used for recording lower leg frontal-plane positions.

7. The method of claim 6, wherein the markers comprise retroreflective tracking markers and the video system comprises a video camera or a gaming system.

8. The method of claim 1, wherein vision software is used for recording lower leg frontal-plane positions.

9. The method of claim 1, wherein one or more pressure or force sensors are positioned in the neutral footwear and the wedged footwear for recording the vertical load.

10. The method of claim 1, wherein inertial sensors located on or about a knee location and an ankle location of a user are used for recording lower leg frontal-plane positions.

11. The method of claim 1, wherein two-dimensional kinematic position data for the one or more wedged footwear and the neutral footwear is used to predict knee adduction moment response.

12. The method of claim 1, further comprising the step of selecting a wedged or non wedged footwear based on predicted knee adduction moment response.

13. The method of claim 12, wherein a computer algorithm is used for selecting the type of footwear for an individual based on the predicted knee adduction moment response.

14. A method for predicting a biomechanical response to a wedged insole, consisting of:
   recording data consisting of vertical load data of an individual taking a single step in neutral footwear, wherein one or more pressure or two-dimensional force sensors are positioned in the neutral footwear for recording vertical load;
   recording vertical load data of the individual taking another single step in one or more types of wedged footwear, wherein the one or more pressure or force sensors are positioned in the wedged footwear for recording vertical load;
   recording lower leg frontal-plane positions of the individual for each type of footwear, using inertial sensors positioned on or about a knee location and an ankle location of the individual;
   identifying a time at which the vertical load is at its maximum during a stance phase for each type of footwear;
   calculating mediolateral positions of the lower leg and foot center of mass for each type of footwear, using the lower leg frontal-plane positions at the time when the vertical load is at its maximum during the stance phase for each type of footwear;
   calculating percent change in the mediolateral positions of the wedged footwear relative to the neutral footwear;
   applying one or more regression equations to predict a knee adduction moment response for the individual; and
   selecting wedged or non-wedged footwear based on predicted knee adduction moment response.

* * * * *